(12) United States Patent
Oh et al.

(10) Patent No.: US 12,188,076 B2
(45) Date of Patent: Jan. 7, 2025

(54) SELECTIVE MEDIUM COMPOSITION FOR DETECTION OF P. CAROTOVORUM AND DETECTION METHOD USING THE SAME

(71) Applicant: KOOKMIN UNIVERSITY INDUSTRY ACADEMY COOPERATION FOUNDATION, Seoul (KR)

(72) Inventors: Se-Wook Oh, Seoul (KR); Unji Kim, Seoul (KR); Ji Hye Baek, Namyangju-si (KR); So-Young Lee, Yangju-si (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 17/968,831

(22) Filed: Oct. 19, 2022

(65) Prior Publication Data
US 2023/0227886 A1    Jul. 20, 2023

(30) Foreign Application Priority Data

Jan. 17, 2022  (KR) ................. 10-2022-0006269
Mar. 29, 2022  (KR) ................. 10-2022-0038487

(51) Int. Cl.
C12Q 1/04    (2006.01)
C12N 1/20    (2006.01)
C12Q 1/10    (2006.01)

(52) U.S. Cl.
CPC ............... *C12Q 1/10* (2013.01); *C12N 1/20* (2013.01); *C12N 2500/05* (2013.01); *C12N 2500/34* (2013.01)

(58) Field of Classification Search
CPC ........ C12Q 1/10; C12N 1/20; C12N 2500/05; C12N 2500/34
See application file for complete search history.

(56) References Cited

FOREIGN PATENT DOCUMENTS

KR    10-2011-0058596 A    6/2011

OTHER PUBLICATIONS

Pedron, Jacques J., et al. "*Pectobacterium aquaticum* sp. nov., isolated from waterways." International Journal of Systematic and Evolutionary Microbiology 69.3 (2019): 745-751 (Year: 2019).*
Andrea Prinzi and Rodney Rohde, Why differential and selective media remain invaluable tool, American Society for Mircobiology, 2020 (Year: 2020).*
Biolog Gen III Microplate, 2015 (Year: 2015).*
Hélias, V., et al. "Two new effective semiselective crystal violet pectate media for isolation of Pectobacterium and Dickeya." Plant pathology 61.2 (2012): 339-345 (Year: 2012).*

(Continued)

*Primary Examiner* — Louise W Humphrey
*Assistant Examiner* — Mary A Crum
(74) *Attorney, Agent, or Firm* — Revolution IP, PLLC (57) ABSTRACT

A medium composition for detection of *P. carotovorum* includes pectin, cellobiose, and inositol as active ingredients. *P. carotovorum* is highly likely to cause soft rot during cultivation as well as storage and transportation such that continuous monitoring is required. In order to solve the issues, the medium composition ensures remarkably outstanding selectivity for *P. carotovorum*.

8 Claims, 8 Drawing Sheets

(56) References Cited

OTHER PUBLICATIONS

Cibrario, Alice, et al. "Carbohydrate metabolism in Oenococcus oeni: a genomic insight." BMC genomics 17.1 (2016): 1-19 (Year: 2016).*
John Bonkowski et al. Pectobacterium carotovorum, wiki.bugwood.org/Pectobacterium_carotovorum, published Jul. 2016 (Year: 2016).*

* cited by examiner

SELECTIVE MEDIUM COMPOSITION FOR DETECTION OF P. CAROTOVORUM AND DETECTION METHOD USING THE SAME

CROSS-REFERENCE TO RELATED APPLICATION

This application claims the benefit of Korean Patent Application No. 10-2022-0006269 filed on Jan. 17, 2022 and No. 10-2022-0038487 filed on Mar. 29, 2022, in the Korean Intellectual Property Office, the entire disclosure of which is incorporated herein by reference for all purposes.

BACKGROUND

1. Field of the Invention

The present disclosure provides a selective medium composition for detection of *Pectobacterium carotovorum* subsp. (*P. carotovorum*) and a detection method using the same.

2. Description of the Related Art

Soft rot occurs during plant growth, accompanied with blackleg and rot while plants becomes soft with peculiar odor due to melting of pectin. In particular, *Pectobacterium carotovorum* subsp. (*P. carotovorum*) destroys plant cell walls through a powerful enzymatic mechanism, causing soft rot during cultivation as well as storage and transportation. Thus, soft rot is reported as the 10 most important bacterial pathogens in agriculture that limits crop yield and quality. In addition, recently, the damage by soft rot in Chinese cabbage has spread nationwide, bringing about many cases of economic damage in many farms. Thus, there is a need for a method for controlling soft rot. However, chemicophysical methods are effective to control soft rot, but are not advisable since it would bring negative effects on the human body during the sterilization process and there are many issues such as tuber development and residual toxic substances. Therefore, it is necessary to isolate and detect soft rot at an early stage to control the same in a timely manner.

According to domestic and foreign studies, in detecting *P. carotovorum* in food, used is a detection method that involves the use of a selective medium after increasing the number of bacteria. In general, a crystal violet pectate (CVP) agar medium is used as a selective medium for detection of *P. carotovorum*.

However, it is known that the conventional selective medium as described above has a limitation in detecting in food due to inability of selectively isolating *P. carotovorum* only. Therefore, research on compositions suitable for competing colonies of *P. carotovorum* is still in progress.

PRIOR ART DOCUMENT

Patent Document (Patent Document 1) Korean Patent Application Publication No. 10-2011-0058596.

SUMMARY

Problem to be Solved by the Invention

An object of the present disclosure is to provide a medium composition for selective detection of *Pectobacterium carotovorum* subsp. (*P. carotovorum*) including pectin, cellobiose, and inositol as active ingredients, and a preparation method thereof.

Another object of the present disclosure is to provide a selective detection method for *P. carotovorum*, including i) inoculating *P. carotovorum* strain into a medium composition for selective detection of *P. carotovorum* in any one of claims 1 to 8 and then culturing the strain; and ii) after inoculation or culture in step i), checking a pattern or circles of color development of colonies formed in the selective medium composition.

Means for Solving the Problem

In order to achieve the above object, the present disclosure provides a medium composition for selective detection of *P. carotovorum*, including pectin, cellobiose, and inositol as active ingredients.

In addition, the present disclosure provides a method of preparing a medium composition for selective detection of *P. carotovorum*, including a) dissolving pectin, cellobiose, inositol, bile salt, and bromocresol green in water and mixing the same; and b) sterilizing the mixture of step a) at 110 to 130° C. for 12 to 18 minutes.

In addition, the present disclosure provides a selective detection method for *P. carotovorum*, including i) inoculating *P. carotovorum* strain into a medium composition for selective detection of *P. carotovorum* in any one of claims 1 to 8 and then culturing the strain; and checking a pattern or circles of color development of colonies formed in the selective medium composition after inoculation or culture in step i).

Effects of the Invention

The present disclosure relates to a medium composition for detection of *P. carotovorum* including pectin, cellobiose, and inositol as active ingredients. The medium composition enables detection of competing colonies of *P. carotovorum* with no involvement of detection using a selective medium after increasing the number of bacteria, thereby facilitating initial control of soft rot.

DETAILED DESCRIPTION

Hereinafter, the present invention will be described in more detail.

With a need to find a way to control plant soft rot, especially to control soft rot by isolating and detecting soft rot at an initial stage since chemicophysical methods may cause negative effects on the human body though they are effective in controlling soft rot bacteria, an example embodiment of the present disclosure was completed, enabling selective detection of *P. carotovorum* without increasing the number thereof.

An example embodiment of the present disclosure provides a medium composition for selective detection of *P. carotovorum*, including pectin, cellobiose, and inositol as active ingredients, wherein the medium composition may further include bile salt and bromocresol green.

The medium composition may further include agar, yeast extract, and sodium chloride (NaCl).

The concentration of the pectin in the medium composition may be 0.01 g/L to 5 g/L.

Figure 1:
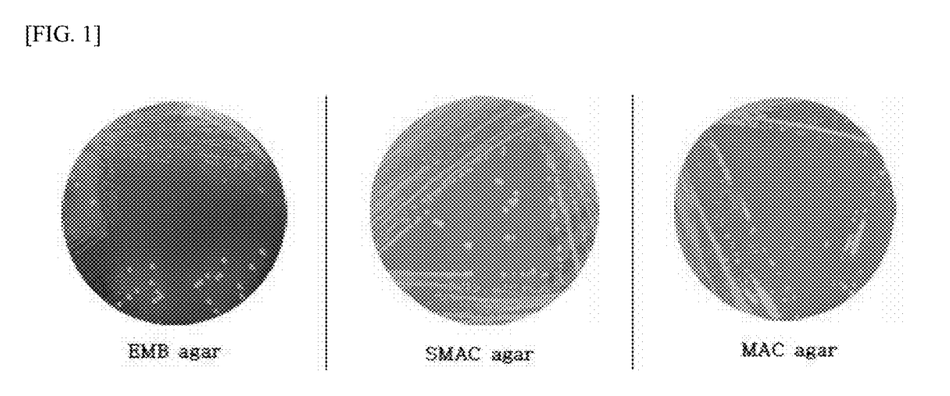
FIG. 1 shows *Pectobacterium carotovorum* subsp. (hereinafter, referred to as *P. carotovorum*) cultured in various *Escherichia coli* (hereinafter, referred to as *E. coli*) selective media.

Pectin, one of components decomposed by *P. carotovorum*, is added as a carbon source. Both *P. carotovorum* and *E. coli* belong to the Enterobacteriaceae and shows high similarity in the sequences, thereby exhibiting a high metabolic similarity of 70% or higher. As shown in FIG. 1, when cultured in EMB, SMAC, and MAC media which are *E. coli* selective media, *P. carotovorum* exhibits the same culture characteristics as *E. coli*.

The concentration of the cellobiose in the medium composition may be 1 g/L to 50 g/L, and the cellobiose may be D-cellobiose.

The D-cellobiose is produced with involvement of endoglucanases and exoglucanases acting on cellulose together, and may be used to distinguish bacteria depending on carbohydrate fermentability. In addition, used as a substrate for BGLU, D-cellobiose may be hydrolyzed to glucose. BGLU, an enzyme that hydrolyzes glycosidic bonds in a carbohydrate moiety, plays a role in decomposing cellobiose into glucose.

The concentration of the inositol in the medium composition may be 0.01 g/L to 1 g/L.

Figure 2:
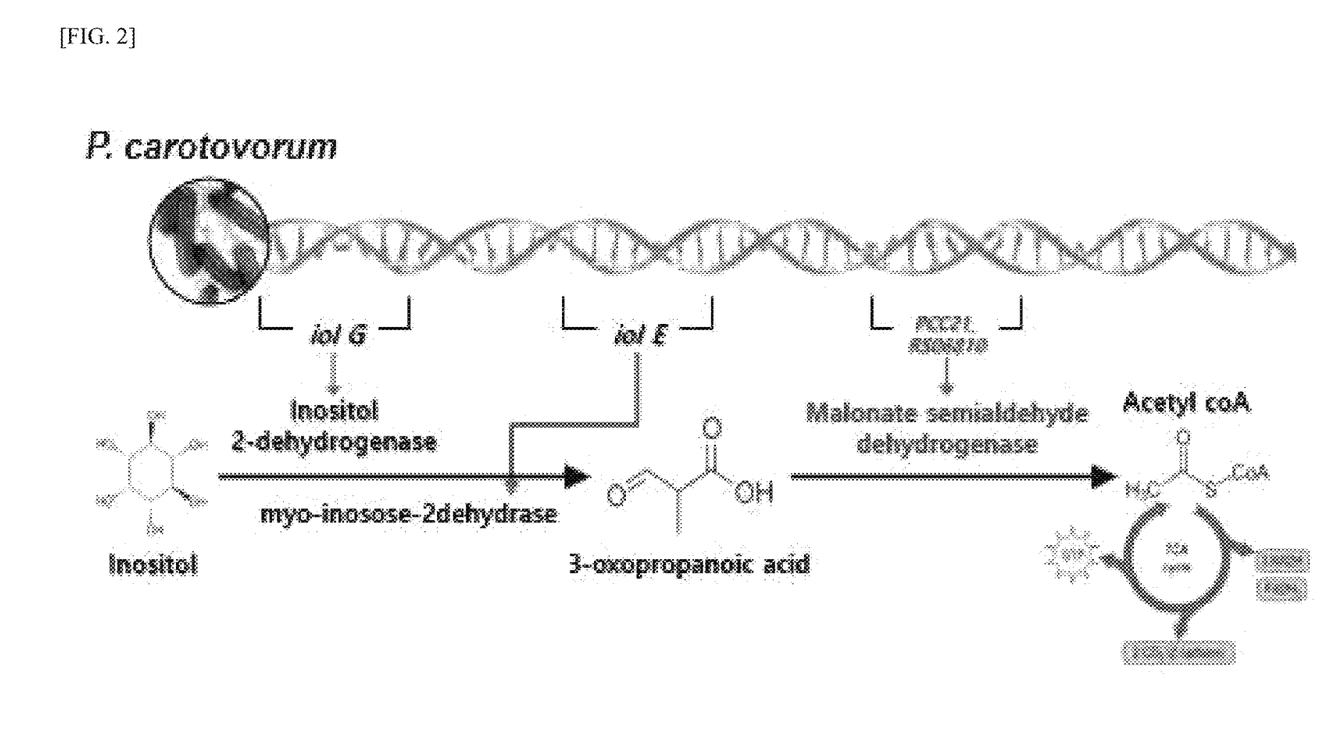
FIG. 2 shows an inositol reduction pathway in *P. carotovorum*.

As shown in FIG. 2, it was found that the inositol was degraded through involvement of operons of *P. carotovorum*.

The bile salt may be added to inhibit the growth of gram-positive bacteria since *P. carotovorum* is a gram-negative bacterium.

The concentration of the bromocresol green in the medium composition may be 0.01 g/L to 0.1 g/L.

The bromocresol green reacts at pH 3.8 to 5.4. Considering that the average pH was 5.03 to 5.07 24 to 48 hours after *P. carotovorum* was cultured in the medium composition while the average pH when *E. coli* and other gram negative bacteria (*Salmonella Typhimurium* and *Dickeya chrysanthemi*) were cultured was 6.5 to 7.09, bromocresol green may be added as a pH indicator for a *P. carotovorum* selective medium.

In addition, an example embodiment of the present disclosure provides a method of preparing a medium composition for selective detection of *P. carotovorum*, including a) dissolving pectin, cellobiose, inositol, bile salt, and bromocresol green in water and mixing the same; and b) sterilizing the mixture of step a) at 110 to 130° C. for 12 to 18 minutes.

In addition, an example embodiment of the present disclosure provides a selective detection method for *P. carotovorum*, including inoculating *P. carotovorum* strain into a medium composition for selective detection of *P. carotovorum* in any one of claims 1 to 8 and then culturing the strain; and ii) after inoculation or culture in step i), checking a pattern or circles of color development of colonies formed in the selective medium composition.

In step i), the strain may be cultured at 27 to 31° C. for 24 to 48 hours.

In step ii), the colonies may have a light yellow-colored center with a cyan-colored periphery.

Hereinafter, example embodiments will be described in detail to help the understanding of the present disclosure. However, the following example embodiments are merely illustrative of the content of the present disclosure, and the scope of the present disclosure is not limited to the following example embodiments. Example embodiments of the present disclosure are provided to more completely explain the present disclosure to those of ordinary skill in the art.

Figure 3:
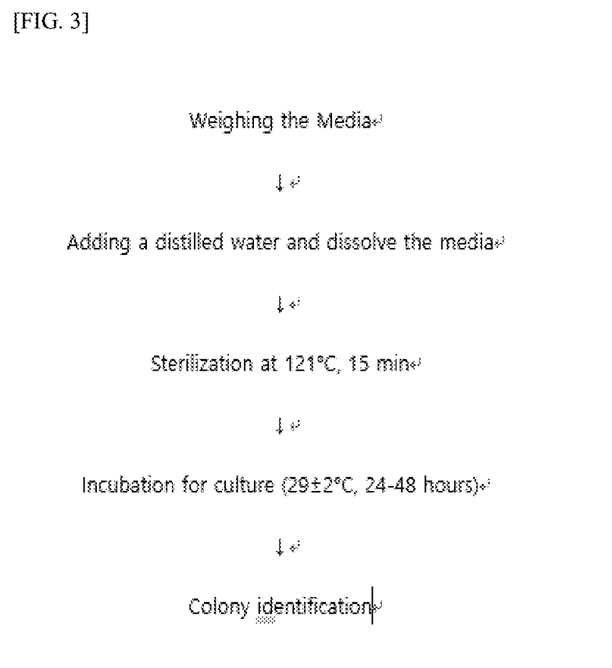
FIG. 3 shows a schematic diagram of a preparation method of a *P. carotovorum* detection medium.

[Preparation Example 1] Basic Composition and Preparation Method of a *P. carotovorum* Detection Medium As shown in FIG. 3, 5 g/L of pectin, 15 g/L of D-cellobiose, 0.1 g/L of inositol, 1.5 g/L of bile salt, 0.04 g/L of bromocresol green, 15 g/L of agar, 10 g/L of yeast extract, and 5 g/L of sodium chloride were firstly dissolved in water, mixed, and sterilized at 121° C. for 15 minutes to complete a *P. carotovorum* detection medium.

[Experimental Example 1] Observation of Colonies

After culturing the *P. carotovorum* strain at 30° C. for 36 hours in the *P. carotovorum* detection medium of Preparation Example 1, colonies in which *P. carotovorum* proliferated were observed.

Figure 4:
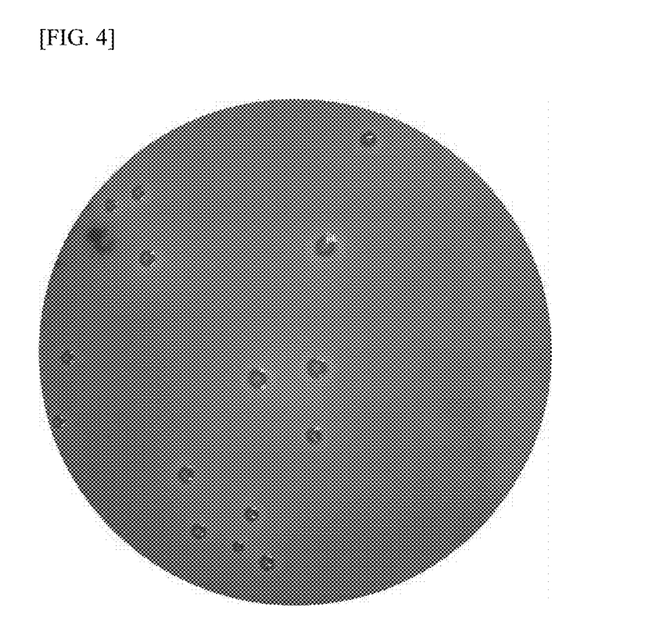
FIG. 4 shows a result of identifying *P. carotovorum* colonies in a *P. carotovorum* detection medium.

As a result, as shown in FIG. 4, it was found that colonies were formed with the light yellow-colored center and the cyan-colored periphery.

[Experimental Example 2] Identification of Specificity of the *P. carotovorum* Detection Medium for *P. carotovorum* Out of 10 Strains In order to identify the selectivity of the *P. carotovorum* detection medium of Preparation Example 1 for various strains, 4 species of gram-positive bacteria (*Listeria monocytogenes, Bacillus subtilis, Bacillus cereus,* and *Staphylococcus aureus*) and 5 species of gram-negative bacteria (*Escherichia coli, Shigella sonnei, Salmonella typhimurium, Pectobacterium carotovorum,* and *Dickeya chrysanthemi*) were cultured in selective media.

Figure 5:
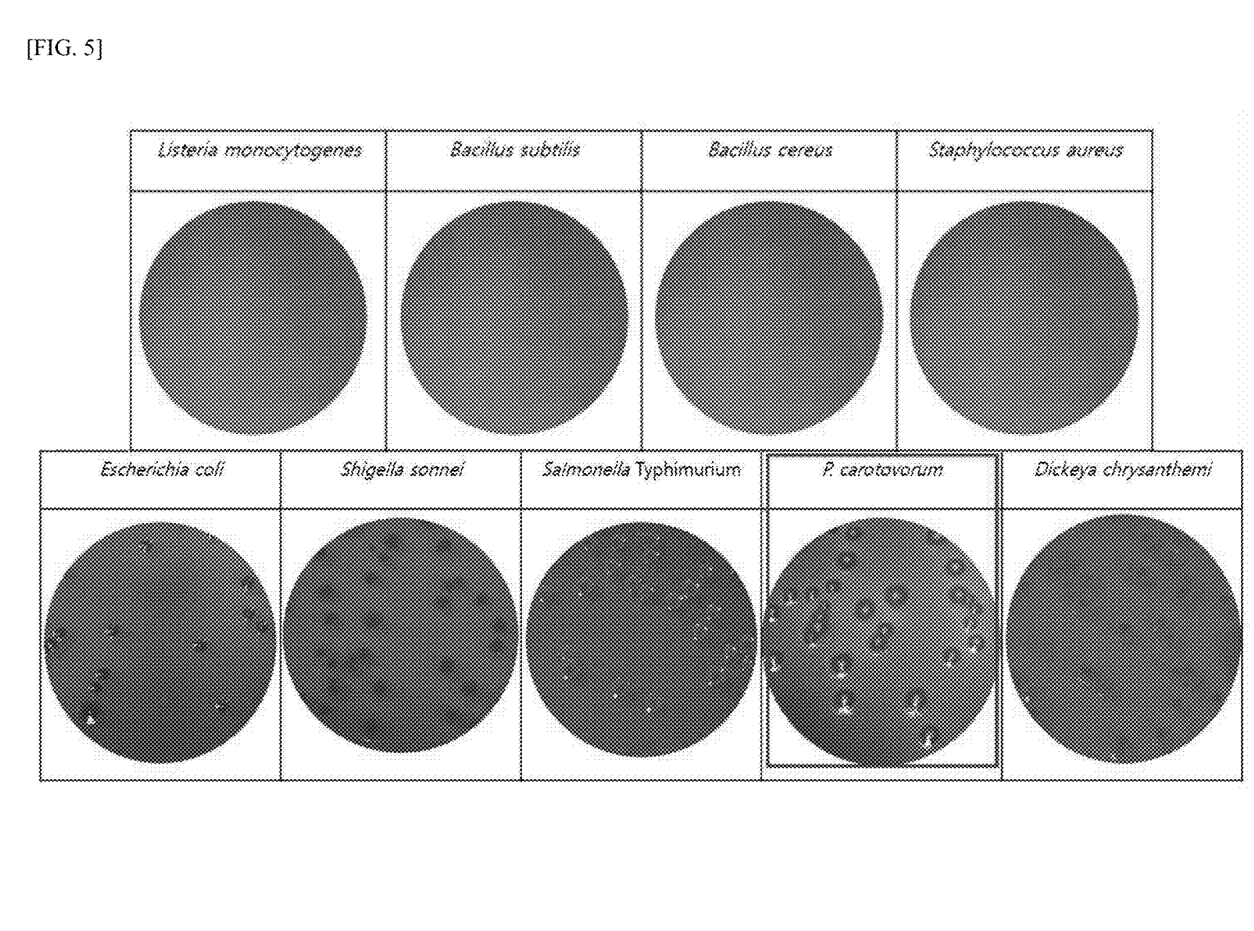
FIG. 5 shows results of comparing *P. carotovorum* colonies with other strains in *P. carotovorum* detection media.

As a result, as shown in FIG. 5, no colonies of gram-positive bacteria were formed due to the inhibited growth by bile salt. In the case of culture of gram-negative bacteria, it was found that colonies with the light yellow-colored center and the dark cyan-colored periphery were formed only when *P. carotovorum* was cultured.

[Experimental Example 3] Identification of Specificity of a Commercialized Medium and a Developed Selective Medium for *P. carotovorum*

In order to identify the specificity of a commercial medium and a *P. carotovorum* detection medium of Preparation Example 1 for *P. carotovorum*, *P. carotovorum* and several competing colonies were mixed and then streaked.

Figure 6:
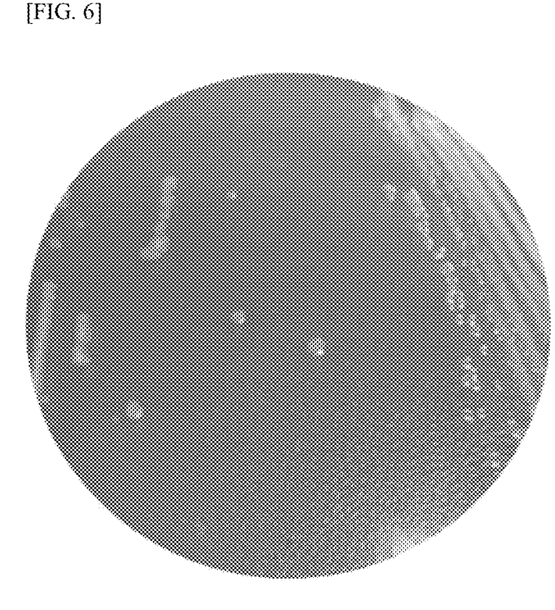
FIG. 6 shows the specificity of *P. carotovorum* for competing colonies in a commercialized CVP medium.
Figure 7:
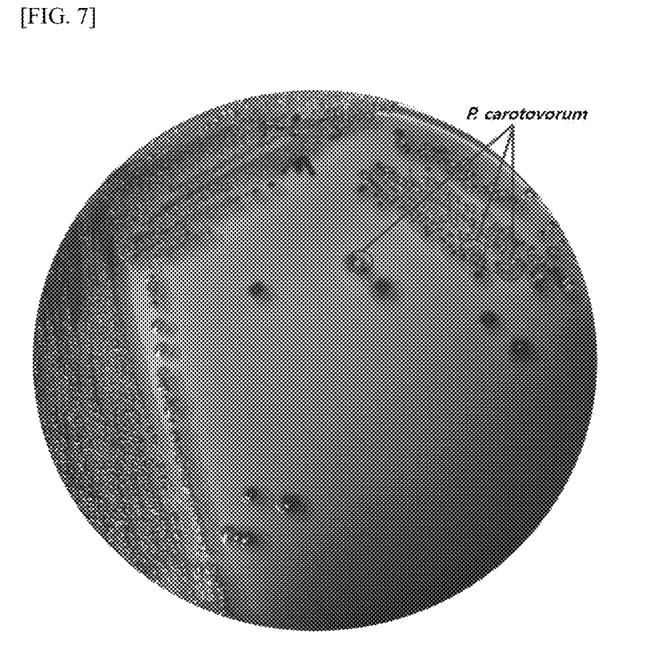
FIG. 7 shows the specificity of *P. carotovorum* for competing colonies in a *P. carotovorum* detection medium.

As a result, as shown in FIG. 6, it was found that isolation was difficult in the CVP medium commercialized for isolating *P. carotovorum* due to the lack of specificity of *P. carotovorum* for competing colonies, while specificity of *P. carotovorum* for competing colonies was derived in the *P. carotovorum* detection medium of Preparation Example 1, as shown in FIG. 7.

[Experimental Example 4] Colony Counting and Isolation Identification after Artificial Inoculation of *P. carotovorum* Into Food After inoculating *P. carotovorum* at a level of 10⁷ CFU/g into 25 g of Chinese cabbage, 225 ml of 0.85% (w/v) sodium chloride (NaCl) solution was added, serial dilutions were performed using 0.85% (w/v) sodium chloride (NaCl) solution, and culture was conducted in the tryptic soy agar (TSA), a nutrient medium, and the *P. carotovorum* detection medium of Preparation Example 1.

Figure 8:
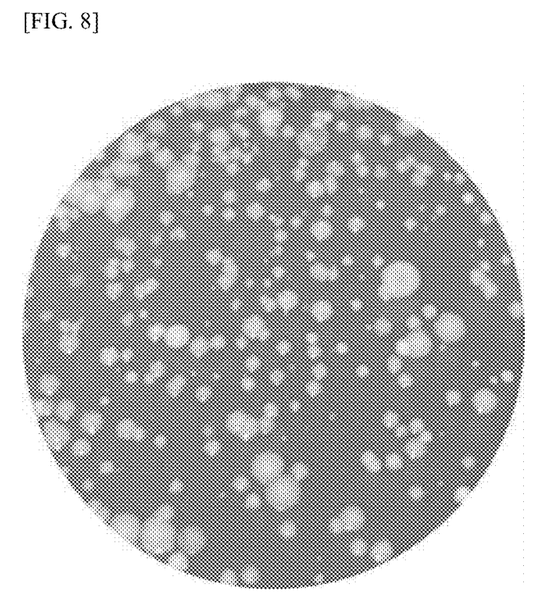
FIG. 8 shows a result of culture in a TSA medium after inoculation of *P. carotovorum* into Chinese cabbage.
Figure 9:
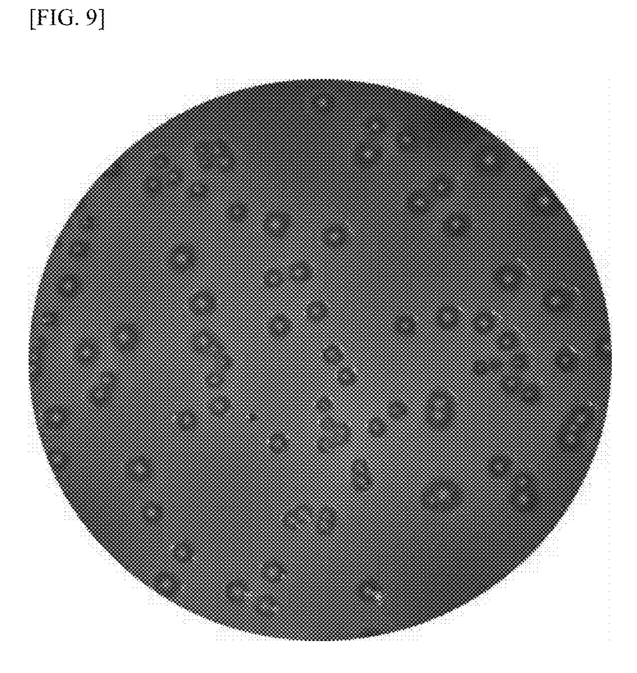
FIG. 9 shows a result of culture in a *P. carotovorum* detection medium after inoculation of *P. carotovorum* into Chinese cabbage.
Figure 10:
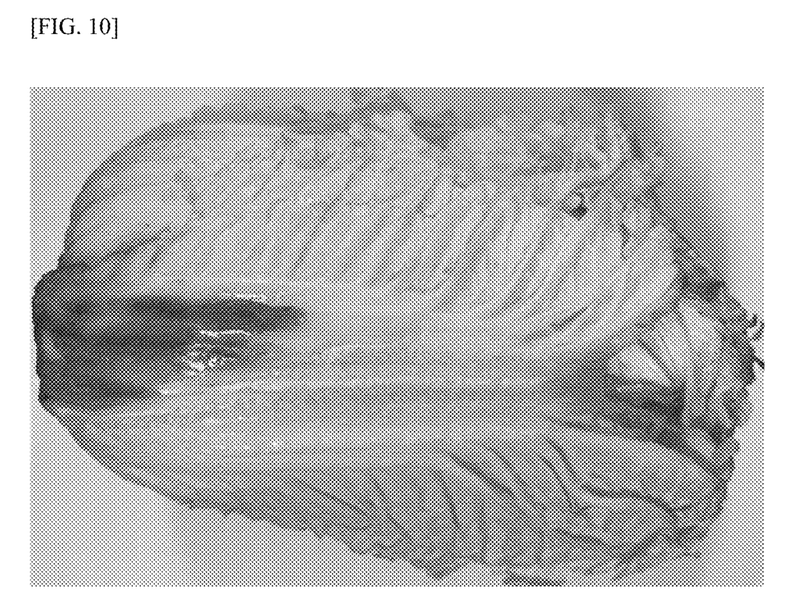
FIG. 10 shows a Chinese cabbage in which soft rot naturally occurred.
Figure 11:
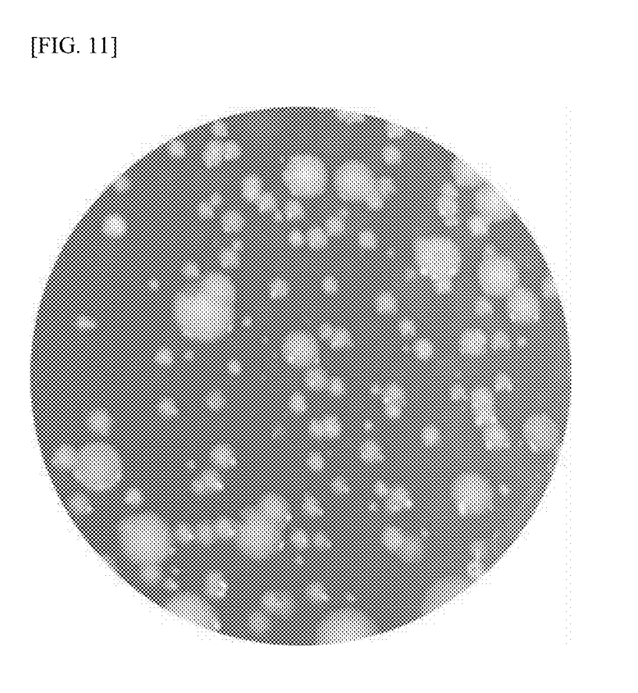
FIG. 11 shows a result of culturing naturally soft rot-occurred Chinese cabbage in a TSA medium.
Figure 12:
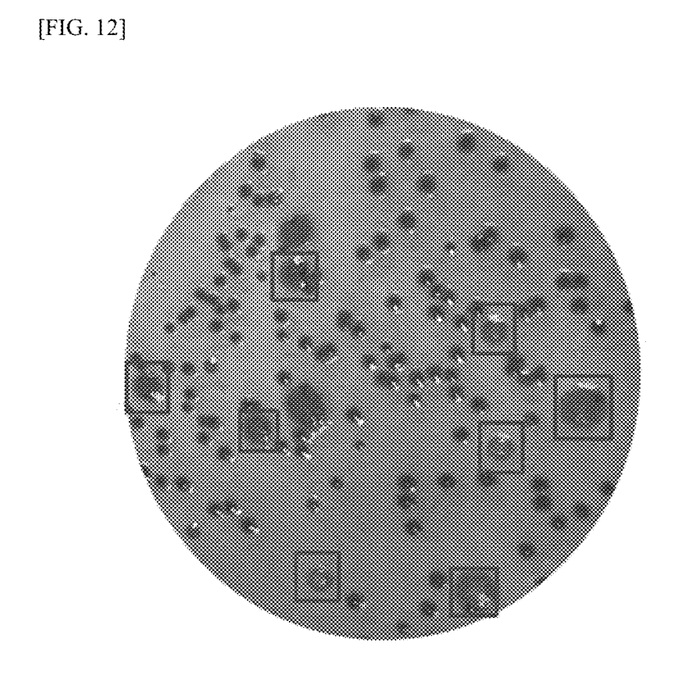
FIG. 12 shows a result of culturing naturally soft rot-occurred Chinese cabbage in a *P. carotovorum* detection medium.

As a result, as shown in FIG. 8, since various bacteria present in food also grew together, counting of only *P. carotovorum* colonies failed. However, as shown in FIG. 9, it was found that colony counting and isolation were possible in the *P. carotovorum* detection medium of Preparation Example 1 since only inoculated *P. carotovorum* was able to grow.

[Experimental Example 5] 16s RNA Sequencing Analysis after Isolation of *P. carotovorum* From Food with Naturally Occurred Soft Rot Chinese cabbage (FIG. 10) in which soft rot occurred naturally was cultured in the TSA medium and the *P. carotovorum* detection medium of Preparation Example 1. As a result, as shown in FIGS. 11 and 12, all the bacteria were grown in the TSA medium, but isolation was possible in the *P. carotovorum* detection medium of Preparation Example 1 due to derivation of selectivity for *P. carotovorum.*

Therefore, 16s RNA sequencing analysis was additionally performed after 9 single colonies of *P. carotovorum* were isolated using the *P. carotovorum* detection medium of Preparation Example 1.

As a result, as shown in Table 1, positivity was detected in 8 samples out of 9 samples, determining that the developed selective medium may be suitable as a selective medium capable of isolating and detecting *P. carotovorum* from naturally occurring soft rot.

TABLE 1

| Treatment Result | | | | | | | | |
|---|---|---|---|---|---|---|---|---|
| T1 | T2 | T3 | T4 | T5 | T6 | T7 | T8 | T9 |
| + | + | + | + | + | + | + | + | − |

Detection probability of Pcc: 89%
*Positive: +, Negative: −

The above description of the present disclosure is for illustration, and those of ordinary skill in the art to which the present disclosure pertains may understand that the present disclosure may be easily modified into other specific forms without modifying the technical spirit or essential features of the present disclosure. Therefore, it should be understood that the example embodiments described above are illustrative in all aspects and not restrictive.

The scope of the present disclosure is indicated by the following claims, and all changes or modifications derived from the meaning and scope of the claims and equivalents thereof should be construed as being included in the scope of the present disclosure.

What is claimed is:

1. A selective detection and isolation method for *Pectobacterium carotovorum* (*P. carotovorum*), the method comprising:
- i) inoculating *P. carotovorum* strain into a medium composition consisting of water, pectin, cellobiose, inositol, bile salt, bromocresol green, agar, yeast extract, and sodium chloride (NaCl) for selective detection of the *P. carotovorum* and then culturing the strain;
- ii) checking a pattern or circles of color development of colonies formed in the selective medium composition after inoculation or culture in step i); and
- iii) selectively isolating the colonies having a light yellow-colored center with a cyan-colored periphery surrounding the light yellow-colored center which indicate the *P. carotovorum* only.

2. The method of claim 1, wherein the strain in step i) is cultured at 27 to 31° C. for 24 to 72 hours.

3. The method of claim 1, wherein the cellobiose is D-cellobiose.

4. The method of claim 1, wherein a concentration of the pectin in the medium composition is 0.01 g/L to 5 g/L.

5. The method of claim 1, wherein a concentration of the cellobiose in the medium composition is 1 g/L to 50 g/L.

6. The method of claim 1, wherein a concentration of the inositol in the medium composition is 0.01 g/L to 1 g/L.

7. The method of claim 1, wherein a concentration of the bromocresol green in the medium composition is 0.01 g/L to 0.1 g/L.

8. The method of claim 1, wherein the medium composition is prepared by:
- a) dissolving the pectin, the cellobiose, the inositol, the bile salt, and the bromocresol green, the agar, the yeast extract, and the sodium chloride (NaCl) in water and mixing the same; and
- b) sterilizing the mixture of step a) at 110 to 130° C. for 12 to 18 minutes.

* * * * *